(12) United States Patent
Schleuning et al.

(10) Patent No.: US 6,283,124 B1
(45) Date of Patent: Sep. 4, 2001

(54) VERSATILE COMPRESSION GARMENT

(76) Inventors: Jeff Schleuning, 828 Crescent Moon Dr., North Las Vegas, NV (US) 89031; Marc Sperberg, 339 Faulkner Ct., Henderson, NV (US) 89014

( * ) Notice: Subject to any disclaimer, the term of this patent is extended or adjusted under 35 U.S.C. 154(b) by 0 days.

(21) Appl. No.: 09/569,733

(22) Filed: May 11, 2000

(51) Int. Cl.$^7$ ........................ A61G 15/00
(52) U.S. Cl. ...................... 128/845; 602/19
(58) Field of Search .................. 128/846, 869, 128/873, 874, 875; 602/19; 450/150

(56) References Cited

U.S. PATENT DOCUMENTS

| | | | |
|---|---|---|---|
| 5,161,257 | * 11/1992 | Arensdorf | 2/2 |
| 5,205,815 | * 4/1993 | Saunders | 602/19 |
| 6,049,906 | * 4/2000 | Aldridge | 2/23 |
| 6,062,946 | * 5/2000 | Rosenberg | 450/155 |

* cited by examiner

Primary Examiner—Michael A. Brown
(74) Attorney, Agent, or Firm—Michael G. Petit

(57) ABSTRACT

A compression garment including, in combination, a form-fitting garment portion and one or more compression pads. One or more compression pads are disposed in a receiving pouch or pouches located on the interior surface of the garment. The position of the compression pad or pads is such that they overlie the portion of a body which is desired to be compressed when the form-fitting garment is donned. When performing the surgical procedure of suction lipoplasty it mis desirable to compress the surgical site postoperatively in order to minimize swelling. Following removal of the liposuction cannula the operative site is closed and covered with a surgical bandage. The garment is then fitted onto the body with the compression pad overlying the surgical area. In another embodiment an adhesive surface on the compression pad is adapted to releasably adhere to a portion of the inner body-facing surface of the garment. The ability to move and reposition of the compression pads on the interior surface of a form-fitting garment so as to overlie the surgical site provides a versatile compression garment.

1 Claim, 1 Drawing Sheet

VERSATILE COMPRESSION GARMENT

BACKGROUND OF THE INVENTION

1. Field of the Invention

The present invention discloses a novel therapeutic garment adapted to apply an adjustable, sustainable elastic compression to a portion of the body.

2. Prior Art

Liposuction is a procedure wherein fat is removed from beneath the skin by means of a suction cannula inserted through a incision in the skin. Following liposuction, the tissue that has been traumatized swells as fluids infiltrate the region. For best cosmetic results it is desirable to reduce or minimize the amount of swelling following liposuction. In order to accomplish this goal, various devices, such as compression pads, have been applied directly to the skin and covered by ace bandage or some other elastic compressive means such as a form-fitting garment made from a synthetic elastic fabric. While in situ compression bandaging accomplishes the goal of reducing or eliminating swelling, it requires affixing a compression bandage to the operative site.

Various other constructions have been employed in a post-operative setting to reduce swelling. Such devices include Velcro straps, Velcro straps in combination with a compressible member and/or garments which are worn tightly around the operative site. In this regard, it is particularly desirable to have a garment which can. (a) cover an operative site; (b) be easily donned by the patient following surgery; and (c)has means for adjustably and securely positioning compression pads around the interior surface thereof Such a compression garment is lacking in the prior art.

SUMMARY OF THE INVENTION

It is a first object of this invention to provide a means for applying a compression dressing to an operative site wherein the compression portion is not affixed to the skin.

It is another object of the invention to provide a garment which may be adjustably fitted around the limb of a patient and having means on the inner skin-facing surface thereof for releasably attaching one or more compressive pads.

It is still another object to provide an elastic garment having one or more pockets or pouches on the inner surface thereof disposed substantially over the entire inner portion of the garment wherein the pouches are designed and adapted to accommodate a compressive pad therewithin.

It is still another object of the invention to provide a compression garment comprising an elastic form-fitting garment having a outer surface and an inner skin-facing surface wherein the inner skin-facing surface has means thereon for affixing a compressive pad thereto.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

DESCRIPTION OF THE PREFERRED EMBODIMENTS

Figure 1:
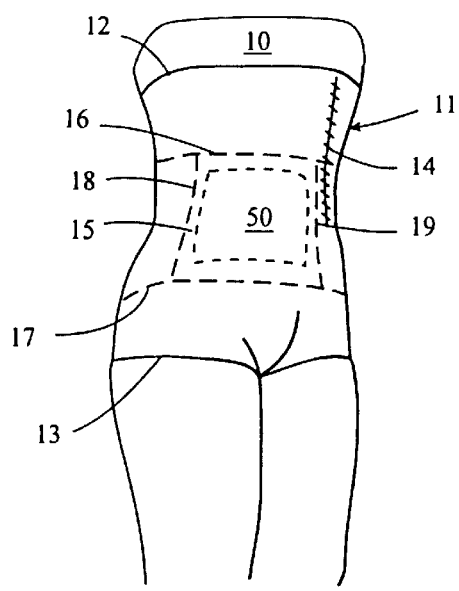
FIG. 1 is a perspective view of a compression garment adapted for the attachment of compressive pads thereto and useful for applying compression to the surgical area abdominal and/or "love-handle" suction lipoplasty.

Turning now to FIG. 1, a patient 10, after undergoing a surgical procedure such as suction lipoplasty of the abdomen, hips or flanks, is shown wearing a compression garment 11 in accordance with the present invention. The compression garment 11 is made from either an elastic or inelastic fabric and extends from above the waist 12 to the upper thigh 13, applying a more or less uniform and relatively small compressive force to the underlying tissue. A slide type of fastener such as a zipper type closure 14 allows the garment 11 to be easily donned and removed. One or more pouches, shown in phantom at numeral 15, has an upper open end 16 and a lower seam 17 which is closed and prevent the downward movement of a compression pad 50 (see FIG. 5) placed within the pouch 15. Two or more vertical seams 18 and 19 further constrain the lateral movement of a compression pad 50 placed within the pouch 15.

Figure 2:
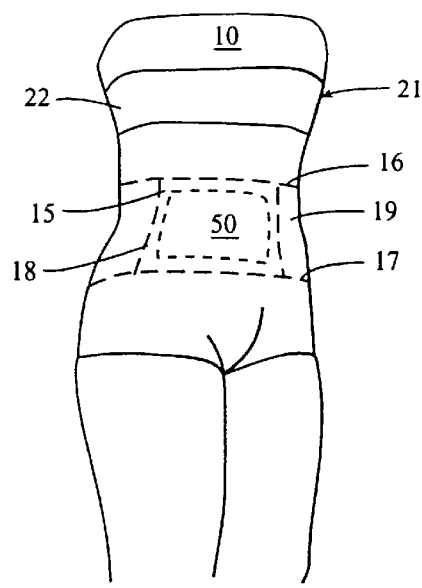
FIG. 2 is a perspective view of a compression garment as shown in FIG. 1 adapted to fit the form presented by a woman's body.

FIG. 2 is a perspective view of a compression garment 21 as shown in FIG. 1 adapted to fit the form presented by a woman's body. The compression garment 21 has a form-fitting garment 22 having one or more pouches 15 sewn inte the inner skin-facing surface of the garment and dimensioned to accommodate one or more compression pads, shown in phantom at numeral 50, placed thereinto. The embodiment 21 of a compression garment in accordance with FIG. 2 is particularly useful for applying compression to a surgical area of a female patient following, abdominal and/or "love-handle" suction lipoplasty.

Figure 3:
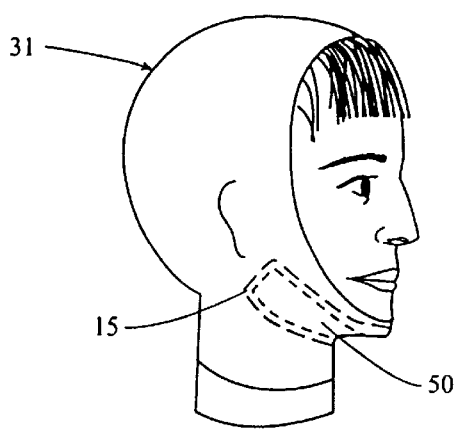
FIG. 3 is a perspective view of a compression garment in accordance with the present invention which is adapted for selectively compressing areas of the head and/or neck following surgery.

FIG. 3 is a perspective view of a compression garment in accordance with the present invention which is adapted for selectively compressing areas of the head and/or neck following surgery. The head and neck compression garment 31 has one or more pouches attached to the inner skin-facing surface thereof, shown in phantom at numeral 15, which are dimensioned to accommodate a compression pad, shown in phantom at numeral 50 in FIG. 3, therewithin.

Figure 4:
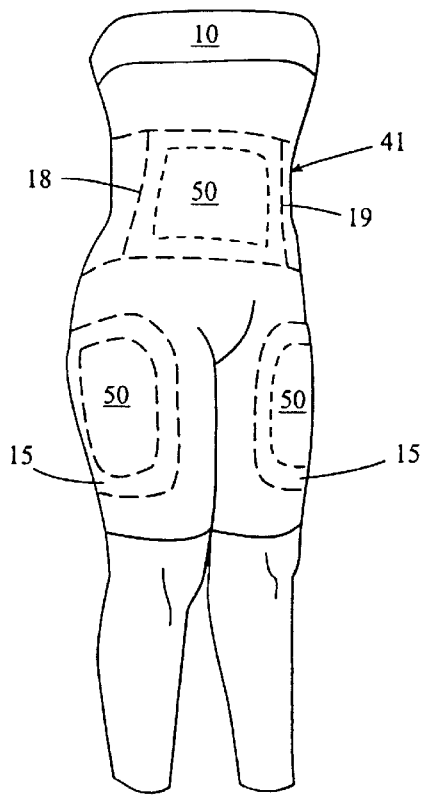
FIG. 4 is a perspective view of a compression garment adapted for the attachment of compressive pads thereto and useful for applying compression to the surgical area following suction lipoplasty of the abdomen, flanks, hips or thighs.

FIG. 4 is a perspective view of a compression garment 41 useful for applying compression to one or more surgical areas following suction lipoplasty of the abdomen, flanks, hips or thighs. The form-fitting garment 41 may comprise a open-mesh elastic fabric or it may comprise a substantially non-extensible fabric provided with one or more slide fasteners to facilitate putting the garment on the body and removal of the garment therefrom. In the event that a non-extensible fabric such as cotton is used to fabricate the garment, when the garment is donned the inner skin-facing surface will not apply substantial compression to any of the underlying tissue. The placement of one or more compression pads 50 in the respective pouches 15 selectively applies substantial differential pressure only to the tissue underlying the compression pad(s) 50.

Figure 5:
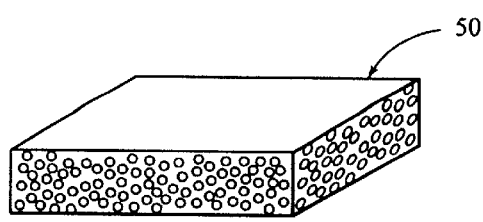
FIG. 5 is a perspective view of a compression pad dimensioned to fit within a pouch on the inner skin-facing surface of a compression garment in accordance with the present invention.

FIG. 5 is a perspective view of a compression pad 50 dimensioned to fit within a pouch 15 disposed on the inner skin-facing surface of one or more of the embodiments of the compression garment in accordance with the present invention. The compression pad 50 consists essentially of a elastically compressible pad. The pad 50 may, for example, comprise a block of a closed-cell elastomeric foam. Compressible pads 50 are made in a variety of sizes to substantially fill the pouch for which they are intended to be inserted. Thus, a compressible pad 50 intended for insertion into a pouch 15 on the skin-facing surface of the embodiment 31 shown in FIG. 3 would be smaller than a compression pad intended for use with the embodiment 11 shown in FIG. 1.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What we claim is:

1. A compression garment adapted for form-fitting attachment to a portion of a body having a form, said portion of said body having traumatized tissue that underlies skin comprising said portion of said body, thereafter to selectively apply differential pressure to said underlying skin covered by said compression garment, said compression garment consisting of at least one elastically compressible compression pad having a shape; and a form-fitting garment having an outer surface and a skin-facing inner surface; said form-fitting garment having at least one pouch affixed to said inner skin-facing surface, said pouch having said shape and dimensioned to snugly accommodate said elastically compressible compression pad therewithin.

* * * * *